United States Patent [19]

Harvey et al.

[11] 4,374,823

[45] Feb. 22, 1983

[54] DENTAL COMPOSITION

[75] Inventors: Kenneth Harvey, Wilmslow; Harry Hayes, Warrington, both of England

[73] Assignee: Colgate-Palmolive Company, New York, N.Y.

[21] Appl. No.: 293,424

[22] Filed: Aug. 17, 1981

[30] Foreign Application Priority Data

Aug. 19, 1980 [GB] United Kingdom ............... 8026943

[51] Int. Cl.³ .......................... A61K 7/16; A61K 7/18
[52] U.S. Cl. ........................................ 424/52; 424/49; 106/208

[58] Field of Search ................... 424/49, 52, 361, 362; 106/205, 208

[56] References Cited

U.S. PATENT DOCUMENTS 3,765,918  10/1973  Jordan et al. ................. 106/205
4,259,316  3/1981  Nakashima et al. ............ 424/52

Primary Examiner—Theodore Morris
Attorney, Agent, or Firm—Robert L. Stone; Murray M. Grill; Herbert S. Sylvester

[57] ABSTRACT

A dentifrice composition is disclosed utilizing a gelling agent consisting essentially of xanthan and guar gums in specified ratios.

5 Claims, No Drawings

DENTAL COMPOSITION

This invention relates to a dental composition. More particularly it relates to a dental composition or toothpaste (including gel) in which a gelling agent mixture is present.

Gelling agents (or binding agents) are mixed with a liquid phase, which typically includes water and/or humectant in order to provide a creamy or gel texture. The most widely used gelling agents include sodium carboxymethyl cellulose and viscarin. However, in some dental creams, these gelling agents are subject to substantial disadvantages. For instance, sodium carboxymethyl cellulose is not compatible with various common dentifrice ingredients such as stannous fluoride and cationic anti-bacterial agents, such as chlorhexidine. Further it can be subject to cellulase attack, particularly in hot climates. Viscarin as the dental cream binder could cause the cream to lose ability to retain the shape of the ribbon extruded from a dental cream tube. Also dental creams containing viscarin can be readily discoloured.

Among the gelling agents which have been proposed in dental creams and related compositions are xanthan and guar gum; prior proposals have been made in British Pat. Nos. 1,372,382 (xanthan); 1,425,922 (xanthan); Japanese published application 7277/67 (xanthan); Japanese published application 28162/72 and U.S. Pat. No. 4,081,526 (each of xanthan and guar gum separately): U.S. Pat. No. 3,723,408 (guar gum); U.S. Pat. No. 4,122,162 (guar gum); U.S. Pat. No. 3,506,757 (xanthamonas colloid).

It is noted that a three component thickener composition containing xanthan and guar gum as well as starch has been proposed in British Pat. No. 1,534,626 as being a useful thickener for printing of textiles, salad dressings and oil well drilling muds. However, in connection with the present invention it has been observed that the three component combination does not provide a desirable creamy or gel character to a dental cream in co-operation with a liquid (water-humectant) system.

According to the present invention, a dental composition comprises an aqueous liquid carrier comprising sorbitol and, proportioned therewith to provide a creamy or gel consistency, a gelling agent composition consisting essentially of xanthan and guar gum, the weight ratio of xanthan to guar gum being at least 1:3.

Despite the many proposals in the prior art for use of xanthan and guar gum independently in dentifrices, there has been no specific proposal for their use combined and we have now found that dentifrices having the specified combination exhibits desirable rheological characteristics of the cream. Such characteristics include proper visocity flow rate, extrusion, ribbon shape retention (or "stand-up") and tube filling ability.

It is a further advantage of this invention that a dental composition containing the gelling agent combination is compatible with other dentifrice components such as stannous fluoride and chlorhexidine.

It is a further advantage of this invention that the dental cream has desirable colour character and is highly white when not pigmented or dyed.

Further advantages will be apparent from consideration of the following.

Xanthan gum is a fermentation product prepared by action of the bacteria of the genus Xanthomonas upon carbohydrates. Four species of Xanthomonas, viz *X. campetris. X. phaseoli, X. malvocearum,* and *X. carotae* are reported in the literature to be the most efficient gum producers. Although the exact chemical structure is not determined, it is generally accepted to be a heteropolysaccharide with a molecular weight of several million. It contains D-glucose, D-mannose, and D-glucuronic acid in the molar ratio of 2.8:3:2.0. The molecule contains 4.7% acetyl and about 3% pyruvate. The proposed chemical structure configuration can be found in McNeely and Kang, Industrial Gums, ed. R. L. Whistler, CH XXI, 2nd Edition, New York, 1973. The procedure for growing, isolating and purifying the xanthan gum is also found in that publication. Further description of xanthan gum is found in Manufacturing Chemist, May 1960, pages 206–208 (including mention at page 208 of potential use of gums therein described for formulating toothpastes).

Guar gum is classed chemically as a galactomannan gum, and is derived from the seed of the guar plant, *Cyanaposis tetragonolobus.* The commercial gum is substantially pure endosperm from that seed. It is particularly useful in the practice of this invention in combination with xanthan as the pure gum; however, derivatives, such as oxidized guar gum, carboxymethylated guar gum and hyroxyalkylated guar gums, are also useful. The hydroxyalkyl guar gum derivatives include hydroxyether and hydroxypropylguar. Further description of guar gum is found in Chapter XIV ("Guar Gum") by Goldstein et al, pages 303–321 of *Industrial Gums,* 2nd Edition by Whistler, Academic Press, New York, San Francisco, London 1973.

As stated, the ratio of xanthan to guar gum used in the invention is at least 1:3; preferably 1:3 to 1:10 by weight. When larger proportions of Xanthan or guar gum are present the combination of flowability and extrusion character and of stand-up of a rheologically desirable dental composition is diminished. In particular when the ratio of xanthan to guar gum is at least about 1:1 and up to about 10:1 by weight or all xanthan, the dental cream is more liquid than is commercially desirable and when the xanthan to guar gum ratio exceeds about 5:1 by weight, stand-up character is substantially diminished. Likewise when guar gum is the only gelling agent, the viscosity, extrusion and stand-up characteristics are diminished.

It is noteworthy that a xanthan-guar gum mixture useful in the present invention is available from Hercules Powder Co. of Wilmington, Delaware and London, England as DP 4-33. The gelling agent of the present invention is employed in the dental composition in amount which provides a creamy or gel consistency. Such amounts are typically about 0.2 to 10% by weight, preferably about 0.5 to 1.5%.

A thickener agent such as silica aerogel may also be included, typically in an amount of 5 to 10% by weight.

The liquid phase, proportioned with the xanthan-guar gum mixture to give a creamy or gel texture, comprises sorbitol humectant, typically commercially available in 70% aqueous solution. Separately added water in addition to that in the sorbitol solution may also be present. Glycerine, a commonly employed dentifrice humectant, is preferably not employed with xanthan-guar gum mixture. However, other humectants, such as low molecular weight polyethylene glycol (e.g. about 200 to 600) or propylene glycol may be used. The total liquid content of the dental composition is generally from 20 to 75% by weight, with sorbitol generally being from 10 to 30% by weight of the dental composition. When a clear gel composition is formed, the amount of water apart from that in the 70% by weight sorbitol solution is generally up to about 5% by weight of the dental composition.

The dental composition further comprises a dentally acceptable water insoluble polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, tri-magnesium phosphate, calcium carbonate, alumina, hydrated alumina, aluminium silicate, zirconium silicate, silica, sodium aluminosilicate (including amorphous silica with combined alumina), bentonite, and mixtures thereof. Preferably polishing materials include insoluble sodium metaphosphate, dicalcium phosphate, silica gel, complex amorphous sodium aluminosilicate and hydrated alumina (e.g. milled alpha-alumina trihydrate).

Alumina particularly the alpha-alumina trihydrate sold by Alcoa as C333, which has an alumina content of 64.9% by weight, a silica content of 0.008% a ferric oxide content of 0.003%, and a moisture content of 0.37% at 110° C., and which has a specific gravity of 2.42 and a particle size such that 100% of the particles are less than 50 microns and 84% of the particles are less than 20 microns, is particularly desirable.

When visually clear gels or clear gels containing an opacifying whitener are employed, a polishing agent of colloidal silica, such as those sold under the trade mark SYOLBLANC (formerly SYLOID) or under the trade mark SANTOCEL as Santocel 100 and sodium aluminosilicate complexes are particularly useful, since they have refractive indices close to the refractive indices of gelling agent-liquid (including humectant) systems commonly used in dentifrices. Such polishing agents may also be used in opaque creams.

Many of the so-called "water-insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, 4th Edition pp. 510-511. The forms of insoluble sodium metaphosphate known as Madrell salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble sodium metaphosphate, may be reduced by washing with water if desired. The insoluble alkali metal metaphosphate is typically employed in powder form of a particle size such that no more than 1% of the material is larger than 37 microns.

The polishing material is generally present in amounts ranging from 15% to 75% by weight of the dental composition.

In certain forms of this invention a fluorine-providing compound is present in the oral preparation. These compounds may be slightly soluble in water or may be fully water-soluble. They are characterised by their ability to release fluoride ions in water and by substantial freedom from reaction with other compounds of the oral preparation. Among these materials are inorganic metal and heavy metal salts, for example, sodium fluoride, potassium fluoride, ammonium fluoride, lead fluoride, a copper fluoride such as cuprous fluoride, zinc fluoride, a tin fluoride such as stannous fluoride or stannous chlorofluoride, sodium fluorosilicate, ammonium fluorosilicate, sodium fluorozirconate, sodium monofluorophosphate, aluminium mono- and difluorophosphate. Alkali metal and tin fluorides, such as sodium and stannous fluorides, sodium monofluorophosphate and mixtures thereof, are preferred. Stannous fluoride a mixture of sodium fluoride and sodium monofluorophosphate are particularly desirable.

The amount of the fluorine-providing compound is dependent to some extent upon the type of compound, and its solubility but it must be a non-toxic amount typically to release a maximum of about 1% by weight of the composition.

Any suitable minimum amount of such compound may be used, but it is preferable to employ sufficient compound to release from about 0.005% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 1%. In the case of sodium monofluorophosphate, the compound may be present in an amount up to 7.6% by weight, more typically 0.76%. When present in mixture the ratio of sodium monofluorophosphate to sodium fluoride is desirably about 1:1 to 3:1 based on fluorine provided by each.

Suitable surface active or detersive material may be included in the dentifrice compositions. Such compatible materials are desirable to provide additional detersive, foaming and antibacterial properties depending upon the specic type of surface active material and are selected similarly. These detergents are water-soluble organic compounds usually, and may be anionic, nonionic or cationic in structure. It is preferred to use the water-soluble non-soap or synthetic organic detergents usually. Suitable detersive materials are known and include, for example, the water-soluble salts or higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate) higher fatty acid esters of 1,2-dihydroxy propane sulphonate (e.g. sodium coconut fatty acid ester of 1,2-dihydroxy propane sulphonate), aliphatic alcohol, ethoxylated sulphates and the like.

The dental cream composition may also contain at least one of the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-amino-propanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compounds", "sarcoside", and the like refers to such compounds having a free carboxylic group or the water-soluble carboxylic salts.

Such materials are utilized in pure or subtantially pure form. They should be as free as practical from soap or similar higher fatty acid material which tends to reduce the activity of these compounds. In usual practice, the amount of such higher fatty acid material is less than 15% by weight of the amide and insufficient to substantially adversely affect it, and preferably less than about 10% of the said amide material.

The various surface active materials may be used in any suitable amount, generally from 0.5 up to 10% by weight, with about 1.5 to 2% especially preferred.

For some purposes it may be desirable to include antibacterial agents in the compositions of the present invention. It is a noteworthy feature of this invention that the xanthan-guar gum mixture is compatible with such antibacterial agents (e.g. 1,6-di-p-chlorophenyl biguanide hexane). Typical antibacterial agents, which may be used in amounts of 0.01 to 5%, preferably 0.05 to 1.0%, by weight of the dentifrice composition include:

$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidehexhane;
1-(lauryldimethylammonium)-8-(p-chlorobenzyldimethylammonium)octane dichloride;
5,6-dichloro-2-guanidinobenzimidazole;
$N^1$-p-chlorphenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavour and sweetening agent may together comprise from about 0.01 to 5% or more of the instant invention.

Various other materials may be incorporated in the dental creams of this invention. Examples thereof are colouring or whitening agents, preservatives, silicones, chlorophyll compounds and ammoniated materials such as urea, diammoniumphosphate and mixtures thereof. These adjuvants are incorporated in the instant compositions in amounts which do not substantially adversely affect the properties and characteristics, suitably selected and used in proper amount depending upon the particular type of preparation involved.

The dental composition should have a pH practical for use, ranging from acidic to alkaline, e.g. a pH of 3 to 10, preferably from 3 to 7 and most preferably from 3 to 5. The reference to the pH refers to a pH determination directly on the dental composition.

Flow characteristics of dental creams or gels can be evaluated by extruding the composition from an aluminium toothpaste tube with the application of a controlled degree of pressure for a specific time, e.g. from 10 to 60 seconds. "Stand-Up" can be evaluated by observing the extended ribbon or cream or gel for a specific time e.g. from 10 to 60 seconds.

The following specific Examples illustrate the present invention. The compositions are typically prepared by adding the xanthan-guar gum mixture to a pre-mix of liquid (typically water and humectant) and heated (e.g. from 35° to 60° C.) with proportioning the ingredients to a creamy or gel consistency. Additional ingredients are then added. The amounts of the various ingredients are by weight unless otherwise indicated. They are then deaerated, flavour is introduced and the compositions are packed in toothpaste tubes.

EXAMPLE 1

A dental cream (A) and a Clear Gel (B) are made up as follows:

| INGREDIENTS | A PARTS | B PARTS |
| --- | --- | --- |
| Sorbitol (70%) | 23.000 | 73.350 (non-crystalising Sorbitol) |
| Xanthan-guar gum (Hercules DP 4-33) | 1.400 | 0.300 |
| Saccharin acid | 0.140 | 0.200 |
| Water | 22.683 | — |
| Insoluble sodium metaphosphate | 45.000 | — |
| Amorphous silica with combined alumina | — | 17.000 |
| Titanium dioxide | 0.400 | — |
| Ascorbic acid | 0.400 | — |
| Silica Aerogel (Syloid 244) | — | 6.500 |
| Stannous fluoride | 0.620 | — |
| Sodium lauryl (3-ethoxylated) sulphate (28% solution) | 5.357 | — |
| Sodium Lauryl Sulphate | — | 1.500 |
| Flavour | 1.000 | 1.000 |
| Colour | — | 0.150 |

The dental cream and clear gel each have good colour and rheological characteristics, particularly including desirable flow and stand up.

Further the gelling agent is compatible with stannous fluoride in dental cream A.

EXAMPLE 2

The following dental creams are prepared with the gelling agent being as indicated below (A-1 to 7 & B,C,D,E and F)

| INGREDIENTS | PARTS |
| --- | --- |
| Sorbitol (70%) | 23.000 |
| Gelling Agent (as indicated) (A-1 to 7 -B-F) | 1.400* |
| Saccharin Acid | 0.140 |
| Water | 22.683* |
| Insoluble sodium metaphosphate | 45.000 |
| Titanium Dioxide | 0.400 |
| Ascorbic Acid | 0.400 |
| Stannous fluoride | 0.620 |
| Sodium lauryl (3-ethoxylated sulphate) (28% solution) | 5.357 |

| INGREDIENTS | PARTS |
| --- | --- |
| Flavour | 1.000 |

*In the Dental Cream using gelling agent C (guar gum), 1 part of gelling agent and 23.083 parts of water are present and in Dental Cream using gelling agent E (starch), 4.500 parts of gelling agent and 19.583 parts of water are present.

The gelling agent variants are as follows:

| GELLING AGENT | RATIO |
| --- | --- |
| A. Xanthan-Guar Gum (X-G) | |
| 1. | 10:1 |
| 2. | 5:1 |
| 3. | 3:1 |
| 4. | 1:1 |
| 5. | 1:3 |
| 6. | 1:5 |
| 7. | 1:10 |
| B. Xanthan | |
| C. Guar gum | |
| D. Xanthan/Guar gum/Starch (X-G-S) | 40:25:35 |
| E. Starch | |
| F. Viscarin | |

It is observed that when the ratio of xanthan to guar gum is at least 1:3 colour and extrusion is excellent. With ratios of xanthan to guar gum of 1:5 or more (e.g. at 1:10) a "levelling off" is observed. Xanthan alone, guar gum alone and starch alone and xanthan-guar gum-starch mixture result in the dental cream having a more liquid consistency, (they flow more rapidly than is desired). Likewise, Viscarin, a conventional gelling agent, is observed to result in a thin dental cream of lower viscosity and stand-up character.

We claim:

1. A dental composition comprising 20 to 75% by weight of an aqueous liquid carrier consisting essentially of sorbitol as humectant and, proportioned therewith to provide a creamy or gel consistency in amount of 0.2 to 10% by weight, a gelling agent composition consisting essentially of xanthan and guar gum, the weight ratio of xanthan to guar gum being from 1:3 to 1:10.

2. A dental composition as claimed in claim 3 wherein the gelling agent composition is present in amount in the range 0.5 to 1.5% by weight.

3. A dental composition as claimed in any of the preceding claims wherein from 15 to 75% of a dentally acceptable water insoluble polishing material is present.

4. A dental composition as claimed in any of the preceding claims wherein a fluorine-providing compound is present in a non-toxic amount to provide up to about 1% fluorine.

5. A dental composition as claimed in claim 4 wherein the fluorine-providing compound is stannous fluoride.

* * * * *